United States Patent
Patt

(10) Patent No.: US 7,384,916 B2
(45) Date of Patent: Jun. 10, 2008

(54) METHODS AND COMPOSITIONS FOR PREVENTING AND TREATING AGING OR PHOTODAMAGED SKIN

(75) Inventor: Leonard M. Patt, Seattle, WA (US)

(73) Assignee: ProCyte Corporation, Redmond, WA (US)

( * ) Notice: Subject to any disclaimer, the term of this patent is extended or adjusted under 35 U.S.C. 154(b) by 0 days.

(21) Appl. No.: 11/376,728

(22) Filed: Mar. 15, 2006

(65) Prior Publication Data

US 2006/0246029 A1  Nov. 2, 2006

Related U.S. Application Data

(60) Provisional application No. 60/662,577, filed on Mar. 16, 2005.

(51) Int. Cl.
*A61K 8/64* (2006.01)
*A61K 31/07* (2006.01)
*A61K 31/45* (2006.01)
*A61K 31/28* (2006.01)
*A61K 31/4415* (2006.01)
*A61K 38/02* (2006.01)
*A61K 38/00* (2006.01)

(52) U.S. Cl. ............... 514/6; 514/2; 514/18; 514/21; 514/169; 514/492; 930/25; 424/59; 424/62; 424/70.14; 424/401

(58) Field of Classification Search ............ None
See application file for complete search history.

(56) References Cited

U.S. PATENT DOCUMENTS

| | | | | |
|---|---|---|---|---|
| 5,118,665 | A * | 6/1992 | Pickart | 514/6 |
| 5,164,367 | A * | 11/1992 | Pickart | 514/6 |
| 5,223,538 | A | 6/1993 | Fridovich et al. | 514/616 |
| 5,227,405 | A | 7/1993 | Fridovich et al. | 514/612 |
| 6,455,088 | B1 | 9/2002 | Dasseux | 426/450 |
| 6,534,549 | B1 | 3/2003 | Newton et al. | 514/772.4 |
| 6,548,690 | B2 | 4/2003 | Mimoun | 556/453 |
| 6,565,873 | B1 | 5/2003 | Shefer et al. | 424/426 |
| 6,565,886 | B1 | 5/2003 | Simonnet et al. | 424/489 |
| 6,572,870 | B2 | 6/2003 | Ribier et al. | 424/401 |
| 6,572,892 | B1 | 6/2003 | Ioulalen et al. | 424/489 |
| 2003/0134781 | A1 * | 7/2003 | Carmichael et al. | 514/6 |
| 2003/0190337 | A1 * | 10/2003 | Bissett | 424/401 |
| 2004/0105894 | A1 | 6/2004 | Gupta | 424/617 |
| 2004/0175347 | A1 * | 9/2004 | Bisset | 424/70.13 |
| 2004/0208903 | A1 * | 10/2004 | Robinson et al. | 424/401 |
| 2006/0018851 | A1 * | 1/2006 | Patt | 424/62 |

FOREIGN PATENT DOCUMENTS

| | | |
|---|---|---|
| DE | 4127790 A1 | 2/1993 |
| DE | 4244418 A1 | 7/1993 |
| DE | 4244415 A1 | 6/1994 |
| WO | WO94/03482 | 1/1994 |
| WO | WO 2006/004787 | 1/2006 |

OTHER PUBLICATIONS

Pickart et al, Journal of Cellular Physiology, 1980, vol. 102, pp. 129-139.*
Iontophoresis from www.wikipedia.org.*
Hyperpigmentation from www.aocd.org/skin/dermatologic_diseases/hyperpigmentation.html.*
Chen, S., et al., "Effects of All-trans Retinoic Acid on Uvb-Irradiated and Non-irradiated Hairless Mouse Skin," *J Invest Dermatol.*, 98(2):248-54, Feb. 1992.
Fitzpatrick, R., et al., "Reversal of Photodamage with Topical Growth Factors: A Pilot Study," *J Cosmet Laser Ther.*, 5(1):25-34, Apr. 2003.
Geesin, J., et al., "Regulation of Collagen Synthesis in Human Dermal Fibroblasts by the Sodium and Magnesium Salts of Ascorbyl-2-phosphate," *Skin Pharmacol.*, 6(1):65-71, 1993.
Hechtman et al., "In *Situ* Activation of Human Erythrocyte Prolidase: Potential for Enzyme Replacement Therapy in Prolidase Deficiency," *Pediatric Research*, 24(6):709-712, 1998.
Kobayashi, T., et al., "Ultrastructural Localization of Superoxide Dismutase in Human Skin," *Acta Derm Venereol.*, 73(1):41-5, Feb. 1993.
Murad S., et al., "Collagen Synthesis in Cultured Human Skin Fibroblasts: Effect of Ascorbic Acid and Its Analogs," *J Invest Dermatol.*, 81(2):158-62, Aug. 1983.
Robert, L., et al., "Effect of L-Fucose and Fucose-rich Polysaccharides on Elastin Biosynthesis, in Vivo and in Vitro," *Biomed Pharmacother.*, 58(2):123-8, Mar. 2004.
Wohlrab, J., et al., "The Influence of L-arginine on the Regulation of Epidermal Arginase," *Skin Pharmacol Appl Skin Physiol.*, 15(1)44-54, Jan.-Feb. 2002.
Chemical Abstracts Database, Accession No. 121:263317, Nov. 26, 1994.

\* cited by examiner

*Primary Examiner*—Anisha Gupta
*Assistant Examiner*—Julie Ha
(74) *Attorney, Agent, or Firm*—Seed IP Law Group PLLC

(57) ABSTRACT

Disclosed are methods for treating aging and photodamaged skin employing topical application of compositions which comprise at least one peptide manganese complex. Also disclosed are methods wherein the composition further comprises retinol, at least one retinol derivative, or a mixture thereof and methods wherein the composition further comprises active agents selected from active drug substances, emollients, sunscreen agents, skin lightening agents, skin protectants, skin conditioning agents, humectants, and mixtures thereof.

17 Claims, No Drawings

METHODS AND COMPOSITIONS FOR PREVENTING AND TREATING AGING OR PHOTODAMAGED SKIN

CROSS-REFERENCE TO RELATED APPLICATION

This application claims the benefit under 35 U.S.C. § 119(e) of U.S. Provisional Patent Application No. 60/662,577 filed Mar. 16, 2005. This application is incorporated herein by reference in its entirety.

BACKGROUND OF THE INVENTION

1. Field of the Invention

The present invention generally relates to the treatment of dermatological conditions and, more specifically, to the treatment of conditions related to aging or photodamaged skin, by topical application of a composition comprising a peptide manganese complex.

2. Description of the Related Art

Aging and photodamage result in a number of changes in the structure and function of skin. Primary among these changes is a thinning of the skin due to lower levels of collagen, elastin and other components of the skin's connective tissue. Lower levels of synthesis and activity (i.e., proliferation and viability) of fibroblasts responsible for the synthesis of collagen and elastin are also characteristic of aging skin.

There are many treatments available to alter the appearance of aging skin, including various creams and oils that primarily serve to rehydrate the skin. Such re-hydration temporarily lessens the appearance of fine line and wrinkles. There are also numerous compounds that enhance the synthesis of certain components of the skin, such as collagen and glycosaminoglycans, and the underlying connective tissue. For example, all-trans retinoic acid has been shown to stimulate collagen synthesis in UVB irradiated skin (see Chen S. et al., *Invest. Dermatol.* 98(2):248–254 (1992)) and topical growth factors have been shown to increase collagen synthesis and produce a thickening of the epidermis (see Fitzpatrick R. E. at al., *Journal of Cosmetic and Laser Therapy* 5(1):25–34 (2003)). Ascorbic acid and its derivatives have also been shown to stimulate increases in collagen synthesis (see Geesin J. C. et al., *Skin Pharmacology* 6(1):65–71 (1993) and Murad S. et al., *J. Invest. Dermatol.* 81(2):158–162 (1983) Furthermore, it has been shown that the biosynthesis of another component of the extracellular matrix, elastin, is increased by topical application of L-fucose or certain fucose-rich polysaccharides (see Robert L. et al., *Biomedicine & Pharmacotherapy* 58(2):123–128 (2004)). Nonetheless, aging skin, and the corresponding fine lines, wrinkles and other external appearances, remain a concern.

Manganese is an essential nutrient involved in the formation of bone and in amino acid, cholesterol, and carbohydrate metabolism. Enzymes, which utilize manganese for activity, include arginase, glutamine synthetase, manganese superoxide dismutase, prolidase, and some carbohydrate transferases. The Adequate Intake levels for men and women have been set at 2.3 and 1.8 mg/day respectively. The enzyme Superoxide Dismutase is one of the most important defenses against oxidative damage in the body. There are two types in humans, namely, the Cu-Zn Superoxide Dismutase (SOD1), which is found mainly in the cytosol of the cell, and the Mn-Superoxide Dismutase (SOD2), which is found in the mitochondria (see Kobayashi et al., *Acta Dermato-Venereologica* 73(1):41–45 (1993)).

Small molecular weight complexes of manganese have been shown to possess superoxide dismutase activity. For example, U.S. Pat. Nos. 5,223,538 and 5,227,405 to Fridovich et al. describe water-soluble manganese complexes useful to reduce and prevent superoxide radical induced toxicity. In addition, U.S. Pat. No. 5,118,665 to Pickart discloses peptide manganese complexes with superoxide dismutase activity useful for enhancing or restoring the resistance of an animal to oxidative or inflammatory damage.

Manganese is also an important component of the enzyme Prolidase. This is a manganese dependent exopeptidase (i.e., a protease which cuts off amino acids from the end of the peptide chain). Prolidase cleaves proline from peptides inside the cell and provides a vital source of proline for new collagen synthesis. The addition of manganese to increase intracellular manganese increases the activity of Prolidase in deficient cells (see Hechtman et al., *Pediatric Research* 24(6):709–712 (1998)). Another manganese requiring enzyme is Arginase. Arginase is an enzyme responsible for the conversion of the amino acid arginine to urea in keratinocytes. The addition of L-arginine and manganese to keratinocyte cultures results in the increase of urea synthesis (see Wohlrab et al., *Skin Pharmacology and Applied Skin Physiology* 15(1):44–54 (2002)).

Although there have been advances in the art, there remains a need for more effective and otherwise improved methods for treating dermatological conditions related to aging or photodamaged skin, such as fine lines and wrinkles. In particular, there remains a need for treatment methods that provide for increased proliferation and viability of dermal fibroblasts and other components of the dermal connective tissue, such as collagen. The present invention addresses these needs and provides further related advantages.

BRIEF SUMMARY OF THE INVENTION

In brief, the present invention is directed to the treatment of dermatological conditions related to aging or photodamaged skin by topical application of a composition comprising at least one peptide manganese complex to an area of affected skin. It has been surprisingly found that such compositions can be used to enhance dermal fibroblast proliferation and viability and to stimulate collagen synthesis, thereby substantially diminishing signs of aging and photodamage in treated skin.

In one embodiment, the present invention is directed to a method for treating aging or photodamaged skin, by contacting an area of skin in need thereof with an effective amount of a composition comprising at least one peptide manganese complex. In a further embodiment, the composition further comprises retinol, a retinol derivative, or a mixture thereof. Topical application of an effective amount of such compositions to areas of skin in need of such treatment results in significant reduction of the signs and symptoms of aging and photodamage found on the areas contacted.

In other further embodiments, the present invention is directed to methods for such treatment wherein the at least one peptide manganese complex is encapsulated in a liposome, microsponge, polymer matrix or other encapsulation technology adapted to aid in the delivery of the peptide manganese complex to the areas of skin need thereof, or to enhance the stability of the composition. In yet other further embodiments, the at least one peptide manganese complex is formulated in an instrument adapted to deliver the peptide manganese complex via iontophoresis or ultrasound to the areas of affected skin.

In yet other further embodiments, the composition further comprises an inert and physiologically-acceptable carrier or diluent, a skin lightening agent, a sunscreen agent, a skin conditioning agent, a skin protectant, an emollient, a humectant, or a mixture thereof in addition to the at least one peptide manganese complex. In other related embodiments, the composition further comprises an active drug substance or an active cosmetic substance.

In still other further embodiments, the composition further comprises an emulsifying agent, a surfactant, a thickening agent, an excipient, or a mixture thereof, and/or the composition is in the form of a liquid, cream, gel, fluid cream, lotion, oil, emulsion or microemulsion.

These and other aspects of this invention will be evident upon reference to the following detailed description of the invention.

DETAILED DESCRIPTION OF THE INVENTION

As noted above, in one embodiment, disclosed is a method for treating aging or photodamaged skin by topically applying, to areas of skin in need thereof, an effective amount of a composition comprising at least one peptide manganese complex. As used herein the word "treat," "treating" or "treatment" refers to using the compositions of the present invention either prophylactically to prevent signs of aging and photodamage, or therapeutically to ameliorate an existing condition characterized by aging or photodamage.

The compositions utilized may be in any form suitable for topical application, including: a liquid, a cream, a lotion, a gel, a fluid cream, an oil, an emulsion or a microemulsion. Some examples of compositions formulated as cosmetic preparations, useful for cleansing and protecting, in addition to treating, skin are: creams for the face, hands, feet, or the entire body (i.e., day creams, night creams, make-up removal creams, and foundation creams); make-up removal formulations; protective or skin care body milks; skin care lotions, gels, or foams (such as cleansing or disinfecting lotions); bath compositions; deodorant compositions; and aftershave and pre-shave gels or lotions.

In more specific embodiments, the at least one peptide manganese complex comprises glycyl-L-histidyl-L-lysine:manganese(II) ("GHK-Mn"), L-alanyl-L-histidyl-L-lysine:manganese(II) ("AHK-Mn"), L-valyl-L-histidyl-L-lysine:manganese(II) ("VHK-Mn"), L-leucyl-L-histidyl-L-lysine:manganese(II) ("LHK-Mn"), L-isoleucyl-L-histidyl-L-lysine:manganese(II) ("IHK-Mn"), L-phenylalanyl-L-histidyl-L-lysine:manganese(II) ("FHK-Mn"), L-prolyl-L-histidyl-L-lysine:manganese(II) ("PHK-Mn"), L-seryl-L-histidyl-L-lysine:manganese(II) ("SHK-Mn"), or L-threonyl-L-histidyl-L-lysine:manganese(II) ("THK-Mn").

As used herein, the abbreviations for the naturally occurring amino acids are:

| | | |
|---|---|---|
| Alanine | Ala | A |
| Arginine | Arg | R |
| Asparagine | Asn | N |
| Aspartic Acid | Asx | D |
| Cysteine | Cys | B |
| Glycine | Gly | G |
| Glutamine | Gln | Q |
| Glutamic Acid | Glu | E |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |

-continued

| | | |
|---|---|---|
| Serine | Ser | S |
| Threonine | Thr | T |
| Tryptophan | Trp | W |
| Tyrosine | Tyr | Y |
| Valine | Val | V |

As used herein, the expression "peptide manganese complex" generally refers to a coordination compound comprising a peptide molecule and a manganese(II) ion non-covalently complexed with the peptide. As is well understood in the art, manganese(II) designates a manganese ion having a valence of 2 (i.e., $Mn^{+2}$). The peptide molecule serves as the complexing agent by donating electrons to the manganese ion to yield the non-covalent complex. The peptide molecule is a chain of two or more amino acid units or amino acid derivative units covalently bonded together via amide linkages, the formation of such linkages being accompanied by the elimination of water.

Generally, an amino acid consists of an amino group, a carboxyl group, a hydrogen atom, and an amino acid side-chain moiety—all bonded, in the case of an alpha-amino acid, to a single carbon atom that is referred to as an alpha-carbon. The amino acid units of the present invention may be provided by amino acids other than alpha-amino acids. For example, the amino acids may be beta- or gamma-amino acids, such as the following:

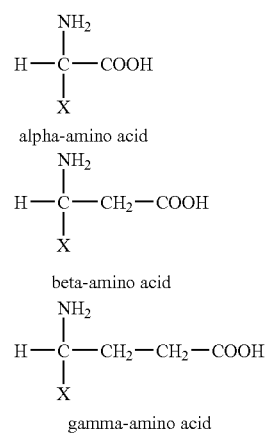

where X is the amino acid side-chain moiety bonded, along with the amino group and hydrogen, to an alpha-, beta-, or gamma-carbon atom.

As another example, the amino acids of the present invention include, but are not limited to, naturally occurring alpha-amino acids. Naturally occurring amino acids are those from which the amino acids units of naturally occurring proteins are derived. Some of these amino acids, along with their respective amino acid side chain moieties, are shown below in Table 1. The naturally occurring amino acids shown are all in the L configuration, referring to the optical orientation of the alpha carbon or other carbon atom bearing the amino acid side chain. A peptide molecule of the present invention may also comprise amino acids that are in the D optical configuration, or a mixture of D and L amino acids.

TABLE 1

Naturally Occurring Amino Acid Side-Chain Moieties

| Amino Acid Side Chain Moiety | Amino Acid |
|---|---|
| —H | Glycine |
| —$CH_3$ | Alanine |
| —$CH(CH_3)_2$ | Valine |
| —$CH_2CH(CH_3)_2$ | Leucine |
| —$CH(CH_3)CH_2CH_3$ | Isoleucine |
| —$(CH_2)_4NH_3^+$ | Lysine |
| —$(CH_2)_3NHC(NH_2)NH_2^+$ | Arginine |
| —$CH_2$-imidazole (HN, N) | Histidine |
| —$CH_2COO^-$ | Aspartic Acid |
| —$CH_2CH_2COO^-$ | Glutamic Acid |
| —$CH_2CONH_2$ | Asparagine |
| —$CH_2CH_2CONH_2$ | Glutamine |
| —$CH_2$-phenyl | Phenylalanine |
| —$CH_2$-phenyl-OH | Tyrosine |
| —$CH_2$-indole | Tryptophan |
| —$CH_2SH$ | Cysteine |
| —$CH_2CH_2SCH_3$ | Methionine |
| —$CH_2OH$ | Serine |
| —$CH(OH)CH_3$ | Threonine |
| Proline ring ($CH_2$—$CH_2$, $CH_2$, NH) | Proline |

Other naturally occurring amino acids include hydroxyproline and gamma-carboxyglutamate.

Representative amino acid derivatives include those set forth in Table 2.

TABLE 2

Amino Acid Derivatives

NH—CH—COOH
|    |
$X_1$  $X_2$ where $X_2$ = H or the following moieties:
—$(CH_2)_nCH_3$ where n = 1 –20
—$(CH_2)_nCH(CH_3)(CH_2)_mCH_3$ where n, m = 0 –20
(when n = 0, m ≠ 0 or 1 and when n = 1, m ≠ 0)
—$(CH_2)_nNH_2$ where n = 1 –20 (n ≠ 4)
—$(CH_2)_nCONH_2$ where n = 3 –20
—$(CH_2)_nCOOH$ where n = 3 –20

 —$(CH_2)_n$-phenyl where n = 2 - 20

TABLE 2-continued

Amino Acid Derivatives

NH—CH—COOH
|    |
$X_1$  $X_2$

—$(CH_2)_n$-phenyl-OH where n = 2 = 2 - 20

—$(CH_2)_n$-indole where n = 2 - 20

—$(CH_2)_nSH$ where n = 2 –20
—$(CH_2)_nS(CH_2)_mCH_3$ where n, m = 1 –20 (when n = 2, m ≠ 0)
—$(CH_2)_nCH_2OH$ where n = 1 –20
—$(CH_2)_nCH(CH_3)OH$ where n = 1 –20,
and where $X_1$ = H or the following moieties:
—$(CH_2)_nCH_3$ where n = 0 –20
—$(CH_2)_nCH(CH_3)(CH_2)_mCH_3$ where n, m = 0 –20.

In addition, histidine derivatives of this invention include compounds having the structure:

where n=1–20, and $Y_1$ and $Y_2$ are independently selected from alkyl moieties containing from 1–12 carbon atoms or aryl moieties containing from 6–12 carbon atoms. In certain embodiments, n is 1, $Y_2$ is methyl, and $Y_1$ is H (i.e., 3-methyl histidyl) or $Y_2$ is H and $Y_1$ is methyl (i.e., 5-methyl histidine).

Similarly, arginine derivatives of this invention include compounds having the structure:

$NH_2$—CH—COOH
         |
       $(CH_2)_n$
         |
         NH
         |
         C=NH
         |
         $NH_2$ where n=1–20 (excluding n=3)

As used herein, "alkyl" means a straight chain or branched, cyclic or noncyclic, substituted or unsubstituted, saturated or unsaturated aliphatic hydrocarbon containing from 1 to 18 carbon atoms. Representative saturated straight chain alkyls include methyl, ethyl, n-propyl and the like; while saturated branched alkyls include isopropyl, sec-butyl, isobutyl, tert-butyl, isopentyl, and the like. Representative, saturated cyclic alkyls include cyclopropyl, cyclobutyl, cyclopentyl, —CH$_2$cyclohexyl, and the like; while unsaturated cyclic alkyls include cyclopentenyl, cyclohexenyl, and the like. Unsaturated alkyls contain at least one double or triple bond between adjacent carbon atoms (referred to as an "alkenyl" or "alkynyl," respectively). Representative alkenyls include ethylenyl, 1-butenyl, isobutylenyl, 2-methyl-2-butenyl, and the like; while representative alkynyls include acetylenyl, 2-butynyl, 3-methyl-1-butynyl, and the like.

Also, as used herein, "aryl" means an aromatic carbocyclic moiety such as phenyl or naphthyl, and may be substituted or unsubstituted. "Arylalkyl," as used herein, means an alkyl having at least one alkyl hydrogen atom replaced with a substituted or unsubstituted aryl moiety, such as benzyl (i.e., —CH$_2$phenyl, —(CH$_2$)$_2$phenyl, —(CH$_2$)$_3$phenyl, —CH(phenyl)$_2$, and the like).

A peptide manganese complex of the present invention may have the formula [R$_1$—R$_2$—R$_3$]:manganese(II) where R$_3$ is at least one amino acid or amino acid derivative, as defined above, bonded to R$_2$ by a peptide bond. Where R$_3$ is a single amino acid or amino acid derivative, then the peptide of the peptide manganese complex is generally classified as a tripeptide. As another example, a peptide manganese complex of the present invention may have the formula [R$_1$—R$_2$—R$_3$]:manganese(II) where R$_3$ is a chemical moiety bonded to the R$_2$ moiety by an amide bond. The expression "chemical moiety," as used herein and with reference to R$_3$, includes any chemical moiety having an amino group capable of forming an amide bond with the carboxyl terminus of R$_2$ (i.e., the carboxyl terminus of histidine, arginine, or derivatives thereof).

As a more particular example, where R$_3$ is a chemical moiety bonded to the R$_2$ moiety by an amide bond, R$_3$ is —NH$_2$, an alkylamino moiety having from 1–20 carbon atoms, or an arylamino moiety having from 6–20 carbon atoms. As used herein, an "alkylamino moiety" encompasses alkyl moieties containing an amino moiety, wherein the alkyl moiety is as defined above, and includes, but is not limited to, octyl amine and propyl amine. Similarly, an "arylamino moiety" encompasses aryl moieties containing an amino moiety, wherein the aryl moiety is as defined above, and includes, but is not limited to, benzylamine and benzyl-(CH$_2$)$_{1-14}$-amine. Further examples of suitable chemical moieties having amino groups capable of forming an amide linkage with the carboxyl terminus of R$_2$ include polyamines such as spermine and sperimidine.

It should be understood that R$_3$ may include more than one chemical moiety. For example, additional amino acids or amino acid derivatives may be bonded to the above-described peptide manganese complexes comprising tripeptides to yield peptide manganese complexes comprising peptides having four or more amino acids and/or amino acid derivatives. For purposes of illustration, Table 3, shown below, presents various representative examples of peptide manganese complexes of the present invention.

TABLE 3

Representative Peptide-Manganese Complexes

Examples of [R$_1$—R$_2$]:manganese(II)

| | |
|---|---|
| glycyl-histidine:manganese | alanyl-histidine:manganese |
| glycyl-(3-methyl)histidine:manganese | alanyl-(3-methyl)histidine:manganese |
| glycyl-(5-methyl)histidine:manganese | alanyl-(5-methyl)histidine:manganese |
| glycyl-arginine:manganese | alanyl-arginine:manganese |
| glycyl-arginine-histidine:manganese | (N-methyl)glycine-arginine:manganese |
| (N-methyl)glycine-histidine:manganese | |

Examples of [R$_1$—R$_2$—R$_3$]:manganese(II)
where R$_3$ is Chemical Moiety Linked by Amide Bond

| | |
|---|---|
| glycyl-histidyl-NH$_2$:manganese | glycyl-arginyl-NH$_2$:manganese |
| glycyl-(3-methyl)histidyl-NH$_2$:manganese | alanyl-(3-methyl)histidyl-NH$_2$:manganese |
| glycyl-arginyl-NH$_2$:manganese | alanyl-arginyl-NH$_2$:manganese |
| (N-methyl)glycine-histidyl-NH$_2$:manganese | (N-methyl)glycine-arginyl-NH$_2$:manganese |
| glycyl-histidyl-NHoctyl:manganese | glycyl-arginyl-NHoctyl:manganese |

Examples of [R$_1$—R$_2$—R$_3$]:manganese(II)
where R$_3$ is Amino Acid or Amino Acid Derivative Linked by Peptide Bond

| | |
|---|---|
| glycyl-histidyl-lysine:manganese | glycyl-arginyl-lysine:manganese |
| glycyl-(3-methyl)histidyl-lysine:manganese | glycyl-(5-methyl)histidyl-lysine:manganese |
| alanyl-histidyl-lysine:manganese | alanyl-arginyl-lysine:manganese |
| alanyl-(3-methyl)histidyl-lysine:manganese | alanyl-(5-methyl)histidyl-lysine:manganese |
| glycyl-histidyl-phenylalanine:manganese | glycyl-arginyl-phenylalanine:manganese |
| glycyl-(3-methyl)histidyl-phenylalanine:manganese | glycyl-(5-methyl)histidyl-phenylalanine:manganese |
| alanyl-histidyl-phenylalanine:manganese | alanyl-arginyl-phenylalanine:manganese |
| alanyl-(3-methyl)histidyl-phenylalanine:manganese | alanyl-(5-methyl)histidyl-phenylalanine:manganese |
| glycyl-histidyl-lysyl-phenylalanyl-phenylalanyl:manganese | glycyl-arginyl-lysyl-phenylalanyl-phenylalanyl:manganese |
| glycyl-(3-methyl)histidyl-lysyl-phenylalanyl-phenylalanyl:manganese | glycyl-(5-methyl)histidyl-lysyl-phenylalanyl-phenylalanyl:manganese |
| (N-methyl)glycyl-histidyl-lysine:manganese | (N-methyl)glycyl-arginyl-lysine:manganese |
| valyl-histidyl-lysine:manganese | glycyl-histidyl-lysyl-prolyl-phenylalanyl-proline:manganese |
| prolyl-histidyl-lysine:manganese | Leucyl-histidyl-lysine:manganese |
| glycyl-D-histidyl-L-lysine:manganese | |
| seryl-histidyl-lysine:manganese | |

In addition, the expression "peptide manganese complex," as used herein, encompasses peptide manganese complex derivatives. The expression "peptide manganese complex derivative," as used herein, refers to a peptide manganese complex where the peptide molecule thereof has: 1) at least one amino acid side chain moiety that is a modification and/or variation of a naturally occurring, amino acid side-chain moiety; and/or 2) at least one of the hydrogens, bonded to an amide linkage nitrogen atom, substituted with a different moiety; and/or 3) the carboxyl group of the carboxyl terminal residue esterified or otherwise modified; and/or 4) at least one hydrogen, bonded to the nitrogen atom of the amino-terminal residue, substituted with a different moiety. Accordingly, the method of the present invention, in another embodiment, employs a composition comprising at least one peptide manganese complex derivative. For example, derivatives of GHK-Mn have the general formula:

[glycyl-histidyl-lysine-R]:manganese(II)

wherein R may be, for example, an alkyl moiety containing from one to eighteen carbon atoms, an aryl moiety containing from six to twelve carbon atoms, an alkoxy moiety containing from one to twelve carbon atoms, or an aryloxy moiety containing from six to twelve carbon atoms.

Further examples of the peptide manganese complex and peptide manganese complex derivatives encompassed by the present invention include, but are not limited to, those disclosed and described in the above- and below-cited U.S. patents that are directed to peptide manganese complexes, as well as those disclosed and described in the published PCT application having the International Publication Number WO 94/03482, which is incorporated herein by reference in its entirety.

The synthesis of the above-described peptide manganese complexes is described in detail in the above-referenced patents. For example, the peptides of the peptide manganese complexes disclosed herein may be synthesized by either solution or solid phase techniques known to one skilled in the art of peptide synthesis. The general procedure involves the stepwise addition of protected amino acids to build up the desired peptide sequence. The resulting peptide may then be complexed to manganese (at the desired molar ratio of peptide to manganese) by dissolving the peptide in water; followed by the addition of manganese chloride or another suitable manganese salt and adjusting the pH to greater than 4.0. The peptide manganese complex thus formed may be used as a solution or as a dry powder after, for example, freeze-drying or spray drying.

The compositions of the present invention may be prepared from aqueous solutions of peptide manganese complexes. Such aqueous solutions are prepared by methods that are well known to those skilled in the art. For example, an amount of dried peptide manganese complex, suitable for a desired concentration, is readily dissolved in water with mixing and gentle heating. An alternative method is to prepare a solution of the desired peptide, followed by the addition of a manganese salt in the desired molar ratio to yield the desired solution of the peptide manganese complex. Examples of manganese salts that may be used are manganese chloride and manganese acetate. When aqueous solutions of peptide manganese complexes are prepared, the solutions are neutralized, typically with NaOH or HCl.

In yet another embodiment of the present invention, the peptide moiety of the at least one peptide manganese complex may be of natural origin. In this embodiment, the peptide is formed by the hydrolysis of naturally occurring proteins, polypeptides, or larger peptides of either plant, microbial, or animal origin. Hydrolysis may be by enzymatic treatment or by acid or base hydrolysis. The manganese complex of this type of peptide manganese complex is formed by addition of a suitable manganese salt to the aqueous solution of the peptide. Alternatively, the peptide manganese complex may be formed during the manufacturing of a formulation by separate additions of the peptide and manganese salt in a suitable solvent.

In more specific embodiments, the composition of the present invention comprises at least one peptide manganese complex, where the concentration of the peptide manganese complex, by weight of the composition, ranges from about 0.01% to about 5%, from about 0.025% to about 1%, or from about 0.05% to about 0.5%, respectively. In other more specific embodiments, the molar ratio of peptide to manganese in the peptide manganese complex ranges from about 1:1 to about 3:1 in some embodiments, and from about 1:1 to about 2:1 in other embodiments. In yet other more specific embodiments, the pH of the composition is from about 4.0 to about 8.0.

In additional embodiments of the method disclosed herein, the composition used comprises at least one peptide manganese complex that is encapsulated in a liposome or microsponge adapted to aid in the delivery of the peptide manganese complex to the area of skin being treated; and, in other embodiments, is formulated in an instrument adapted to deliver the peptide manganese complex via iontophoresis to the area of skin in need of treatment. Exemplary methods of encapsulating pharmaceutical or cosmetic actives are disclosed in the U.S. Pat. Nos. 6,572,892, 6,572,870, 6,565,886, 6,565,873, 6,548,690, 6,534,549 and 6,455,088.

As noted above, in certain embodiments, the composition utilized in the method of the present invention further comprises retinol, a retinol derivative, or a mixture thereof, in addition to a peptide manganese complex. Retinol is also known as vitamin A and has the formula 3,7-dimethyl-9-(2, 6, 6-trimethyl-1-cyclohexen-1-yl)-2,4,6,8-nonatetraen-1-ol.

Other terms that are used for retinol are axerophthol and vitamin A alcohol. In certain specific embodiments of the present invention that use compositions comprising retinol, the isomeric forms of the retinol used are: all-trans-retinol; 1,3-cis-retinol; 3,4-didehydro-retinol; and 9-cis-retinol, respectively. In other specific embodiments of the present invention that use compositions comprising a retinol derivative, the latter is an ester of retinol selected from $C_1$–$C_{30}$ esters of retinol; $C_2$–$C_{20}$ esters of retinol; and $C_2$, $C_3$, and $C_{16}$ esters of retinol, respectively. More specifically, the ester of retinol may be retinyl palmitate, retinyl acetate and retinyl propionate. Other retinol derivatives that may be used are retinoic acid and retinyl aldehyde. The concentration of the retinol, retinol derivative, or mixture thereof, ranges from about 0.001% to about 10% in some embodiments; from about 0.01% to about 1% in other embodiments; and from about 0.01% to about 0.5% in yet other embodiments, by weight of the composition.

In further embodiments of the methods of the present invention, the compositions used may comprise at least one active agent in addition to the peptide manganese complex. In one such embodiment, the composition is formulated as a pharmaceutical preparation and comprises at least one active drug substance, such as a sunscreen active. In another such embodiment, the composition further comprises at least one active agent for rendering the composition suitable as a cosmetic preparation. Active agents, as defined herein, are compounds that provide benefits to the skin and/or provide desirable properties to a composition formulated as a cosmetic preparation. Some examples of active agents, other than drug substances, are skin lightening agents, tanning agents, skin conditioning agents, skin protectants, emollients and humectants.

Representative sunscreen drugs are active ingredients that absorb, reflect, or scatter radiation in the UV range at wavelengths from 290 to 400 nanometers. Specific examples include benzophenone-3 (oxybenzone), benzophenone-4 (sulisobenzone), benzophenone-8 (dioxybenzone), butyl methoxydibenzoylmethane (Avobenzone), DEA-methoxycinnamate (diethanolamine methoxycinnamate), ethyl dihydroxypropyl PABA (ethyl 4-[bis(hydroxypropyl)] aminobenzoate), ethylhexyl dimethyl PABA (Padimate O), ethylhexyl methoxycinnamate (octyl methoxycinnamate), ethylhexyl salicylate (octyl salicylate), homosalate, menthyl anthranilate (Meradimate), octocrylene, PABA (aminobenzoic acid), phenylbenzimidazole sulfonic acid (Ensulizole), TEA-salicylate (trolamine salicylate), titanium dioxide, and zinc oxide. One skilled in the art will appreciate that other sunscreen agents may be used in the compositions and preparations of the present invention.

Representative skin lightening agents include, but are not limited to, ascorbic acid and derivatives thereof, kojic acid and derivatives thereof, hydroquinone and derivatives thereof, azelaic acid, various plant extracts such as those from licorice, grape seed and bear berry, and mixtures of any one or more of the foregoing. Those skilled in the art will appreciate that other skin lightening agents may be included in the compositions used for some of the methods of the present invention.

Hydroquinone (p-dihydroxybenzene or p-hydroxyphenol) is a phenolic compound having the following structure:

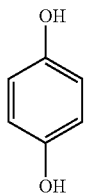

Derivatives of hydroquinone include other substituted phenolic compounds such as N-acetyl-4-S-cysteaminylphenol (4-S-CAP), Arbutin (hydroquinone-beta-D-glucopyranoside), t-butyl hydroquinone:

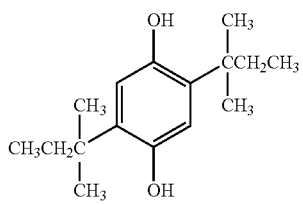

and other alkyl substitutions. Esters of hydroquinone are also possible, such as Hydroquinone mono-methyl ether (p-Hydroxyanisole).

Kojic acid(5-hydoxy-4-pyran-4-one-2-methyl) is a fungal metabolic product having the following structure:

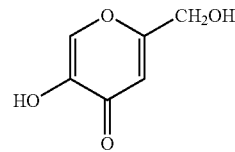

Derivatives of kojic acid consist of fatty acid esters such as kojic acid dipalmitate (Hexadecanoic Acid, 4-Oxo-6-[[(1-Oxohexadecyl)Oxy]Methyl]-4H-Pyran-3-yl Ester):

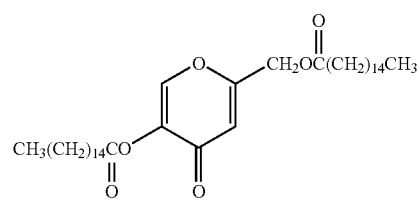

monopalmitate, iso-palmitate, and the like.

As noted above, the compositions may further comprise skin conditioning agents. Such agents comprise substances that enhance the appearance of dry or damaged skin, as well as materials that adhere to the skin to reduce flaking, restore suppleness, and generally improve the appearance of skin. Representative examples of skin conditioning agents include: acetyl cysteine, N-acetyl dihydrosphingosine, acrylates/behenyl acrylate/dimethicone acrylate copolymer, adenosine, adenosine cyclic phosphate, adensosine phosphate, adenosine triphosphate, alanine, albumen, algae extract, allantoin and derivatives, aloe barbadensis extracts, aluminum PCA, amyloglucosidase, arbutin, arginine, azulene, bromelain, buttermilk powder, butylene glycol, caffeine, calcium gluconate, capsaicin, carbocysteine, carnosine, beta-carotene, casein, catalase, cephalins, ceramides, chamomilla recutita (matricaria) flower extract, cholecalciferol, cholesteryl esters, cocobetaine, coenzyme A, corn starch modified, crystallins, cycloethoxymethicone, cysteine DNA, cytochrome C, darutoside, dextran sulfate, dimethicone copolyols, dimethylsilanol hyaluronate, DNA, elastin, elastin amino acids, epidermal growth factor, ergocalciferol, ergosterol, ethylhexyl PCA, fibronectin, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, and kinetin.

Other examples of skin conditioning agents are: lactoferrin, lanosterol, lauryl PCA, lecithin, linoleic acid, linolenic acid, lipase, lysine, lysozyme, malt extract, maltodextrin, melanin, methionine, mineral salts, niacin, niacinamide, oat amino acids, oryzanbl, palmitoyl hydrolyzed proteins, pancreatin, papain, PEG, pepsin, phospholipids, phytosterols, placental enzymes, placental lipids, pyridoxal 5-phosphate, quercetin, resorcinol acetate, riboflavin, RNA, saccharomyces lysate extract, silk amino acids, sphingolipids, stearamidopropyl betaine, stearyl palmitate, tocopherol, tocopheryl acetate, tocopheryl linoleate, ubiquinone, vitis vinifera (grape) seed oil, wheat amino acids, xanthan gum, and zinc gluconate. Skin conditioning agents, other than those listed above, may also be used, as is readily appreciated by those skilled in the art.

In other embodiments, the compositions may include a skin protectant, defined herein as a compound that protects injured or exposed skin or mucous membrane surfaces from harmful or irritating external compounds. Representative examples thereof include: algae extract, allantoin, aluminum hydroxide, aluminum sulfate, betaine, camellia sinensis leaf extract, cerebrosides, dimethicone, glucuronolactone, glycerin, kaolin, lanolin, malt extract, mineral oil, petrolatum, potassium gluconate, and talc. Those skilled in the art will readily appreciate that skin protectants, other than those listed above, may be included in the compositions used for the methods of the present invention.

An emollient, as the term is used herein, is a cosmetic ingredient that can help the skin maintain a soft, smooth, and pliable appearance. Emollients are able to provide these benefits, largely owing to their ability to remain on the skin surface or in the stratum corneum to act as a lubricant and reduce flaking. Some examples of emollients, suitable for embodiments of this invention, are: acetyl arginine, acetylated lanolin, algae extract, apricot kernel oil PEG-6 esters, avocado oil PEG-11 esters, bis-PEG-4 dimethicone, butoxyethyl stearate, $C_{18}$–$C_{36}$ acid glycol ester, $C_{12}$–$C_{13}$ alkyl lactate, caprylyl glycol, cetyl esters, cetyl laurate, coconut oil PEG-10 esters, di-$C_{12}$–$C_{13}$ alkyl tartrate, diethyl sebacate, dihydrocholesteryl butyrate, dimethiconol, dimyristyl tartrate, distearth-5 lauroyl glutamate, ethyl avocadate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, hydroxypropyl bisisostearamide MEA, isostearyl neopentanoate, isostearyl palmitate, isotridecyl isononanoate, laureth-2acetate, lauryl polyglyceryl-6cetearyl glycol ether, methyl gluceth-20 benzoate, mineral oil, myreth-3 palmitate, octyidecanol, octyldodecanol, odontella aurita oil, 2-oleamido-1,3 octadecanediol, palm glycerides, PEG avocado glycerides, PEG castor oil, PEG-22/dodecyl glycol copolymer, PEG shorea butter glycerides, phytol, raffinose, stearyl citrate, sunflower seed oil glycerides, and tocopheryl glucoside. Those skilled in the art will readily appreciate that emollients, other than those listed above, may also be used.

Humectants are cosmetic ingredients that help maintain moisture levels in skin. Some examples of suitable humectants are: acetyl arginine, algae extract, aloe barbadensis leaf extract, betaine, 2,3-butanediol, chitosan lauroyl glycinate, diglycereth-7 malate, diglycerin, diglycol guanidine succinate, erythritol, fructose, glucose, glycerin, honey, hydrolyzed wheat protein/PEG-20 acetate copolymer, hydroxypropyltrimonium hyaluronate, inositol, lactitol, maltitol, maltose, mannitol, mannose, methoxy PEG, myristamidobutyl guanidine acetate, polyglyceryl sorbitol, potassium PCA, propylene glycol, sodium PCA, sorbitol, sucrose, and urea. Other humectants may be used for yet additional embodiments of this invention, as will be appreciated by those skilled in the art.

In addition to the foregoing active agents, the compositions employed in the methods of the present invention may also comprise inert and physiologically acceptable carriers or diluents. Suitable carriers or diluents include, but are not limited to: water, physiological saline, bacteriostatic saline (e.g., saline containing 0.9 mg/ml benzyl alcohol), petrolatum based creams (e.g., USP hydrophilic ointments and similar creams), various types of pharmaceutically acceptable gels, and short chain alcohols and glycols (e.g., ethyl alcohol and propylene glycol).

In other further embodiments, the compositions employed may comprise additional ingredients such as fatty alcohols, fatty acids, organic or inorganic bases, preserving agents (such as phenoxyethanol and mixtures of various parabens), wax esters, steroid alcohols, triglyceride esters, phospholipids such as lecithin and cephalin, polyhydric alcohol esters, fatty alcohol ethers, hydrophilic lanolin derivatives, hydrophilic beeswax derivatives, cocoa butter waxes, silicon oils, pH balancers, cellulose derivatives, hydrocarbon oils such as palm oil, coconut oil, and mineral oil, and mixtures thereof.

Additional ingredients may be included in the above compositions to vary the texture, viscosity, color and/or appearance thereof, as is appreciated by one of ordinary skill in the art. Accordingly, in a further embodiment, the compositions, in addition to at least one peptide manganese complex, comprise an emulsifying agent, a surfactant, a thickening agent, an excipient or a mixture thereof.

More specifically, emulsifiers and surfactants may be included in those compositions used for the present invention that are formulated as emulsions. Either water-in-oil or oil-in-water emulsions may be formulated. Examples of suitable surfactants and emulsifying agents include: nonionic ethoxylated and nonethoxylated surfactants, abietic acid, almond oil PEG, beeswax, butylglucoside caprate, $C_{18}$–$C_{36}$ acid glycol ester, $C_9$–$C_{15}$ alkyl phosphate, caprylic/capric triglyceride PEG-4 esters, ceteareth-7, cetyl alcohol, cetyl phosphate, corn oil PEG esters, DEA-cetyl phosphate, dextrin laurate, dilaureth-7 citrate, dimyristyl phosphate, glycereth-17 cocoate, glyceryl erucate, glyceryl laurate, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPG's, raffinose myristate, sodium caproyl lactylate, sodium caprylate, sodium cocoate, sodium isostearate, sodium tocopheryl phosphate, steareths, TEA-$C_{12}$–$C_{13}$ pareth-3 sulfate, tri-$C_{12}$–$C_{15}$ pareth-6 phosphate, and trideceths. Other surfactants and emulsifiers may be used, as will be appreciated by those skilled in the art.

Examples of thickening (i.e., viscosity increasing) agents include, but are not limited to, those agents commonly used in skin care preparations, such as: acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxytheylcellulose, hydroxypropylcellulose, hydroxpropyl starch, magnesium alginate, methylcellulose, microcrystalline cellulose, pectin, various PEG's, polyacrylic acid, polymethacrylic acid, polyvinyl alcohol, various PPG's, sodium acrylates copolymer, sodium carrageenan, xanthan gum, and yeast beta-glucan. Thickening agents other than those listed above may also be used in related embodiments of the present invention.

As heretofore noted, the compositions used for the methods of the present invention, being products for topical application to human skin, are, accordingly, formulated as a liquid, cream, gel, fluid cream or milk, lotion, oil, emulsion or microemulsion. Also, the above compositions may be further combined with suitable excipients adapted for application to the face and neck. Suitable excipients should have a high affinity for the skin, be well tolerated, stable, and yield a consistency that allows for easy and pleasant utilization.

Typically, for a method of the present invention, aside from the content of the composition used, a small amount of the composition (from about 1 ml to about 5 ml) is applied to exposed areas of skin from a suitable container or applicator, and, if necessary, the composition is then spread over and/or rubbed into the skin using the hand, finger, or other suitable device. Each composition disclosed herein is typically packaged in a container that is appropriate in view of the composition's viscosity and intended use by the consumer. For example, a lotion or fluid cream may be packaged in a bottle, roll-ball applicator, capsule, propellant-driven aerosol device, or a container fitted with a manually operated pump. A cream may simply be stored in a non-deformable bottle, or in a squeeze container, such as a tube or a lidded jar.

The following examples are provided for the purpose of illustration, not limitation.

EXAMPLES

The examples, which follow, illustrate the preparation, characterization and utility of certain compositions used for exemplary embodiments directed to the methods of the present invention; and illustrate the effectiveness of such methods in treating conditions related to aging and photo-damaged skin.

Example 1

The composition of a representative moisturizing lotion used for a method of the present invention is shown below.

Representative Moisturizing Lotion

| Ingredients | % w/w |
|---|---|
| Water | 73.80% |
| Glycerin | 1.00% |
| Hydroxyethylcellulose | 0.50% |
| diisopropyl adipate | 4.00% |
| isocetyl palmitate | 6.00% |
| octyl stearate | 10.00% |
| glyceryl monooleate | 1.00% |
| cetyl alcohol | 1.00% |
| stearyl alcohol | 0.80% |
| behenyl alcohol | 0.50% |
| palmitic acid | 0.25% |
| stearic acid | 0.25% |
| L-alanyl-L-histidyl-L-lysine manganese complex | 0.30% |
| propylene glycol | 0.55% |
| Phenoxyethanol | 0.30% |
| iodopropynyl butylcarbonate | 0.02% |
| total | 100.00% |

Example 2

The composition of a representative moisturizing cream used for a method of the present invention is shown below.

Representative Moisturizing Cream

| Ingredients | % w/w |
|---|---|
| purified water | 77.35% |
| ethylhexyl palmitate | 8.00% |
| Octyldodecanol | 2.50% |

-continued

| Ingredients | % w/w |
|---|---|
| butyloctyl calicylate | 2.00% |
| Squalane | 1.50% |
| jojoba oil | 0.50% |
| tocopheryl acetate | 0.20% |
| Bisabolol | 0.20% |
| Polyacrylamide | 1.50% |
| laureth-7 | 0.50% |
| Glycerin | 3.00% |
| Panthenol | 0.60% |
| Allantion | 0.10% |
| Cyclomethicone | 0.50% |
| Hydroxyethylcellulose | 0.10% |
| polysorbate 20 | 0.20% |
| glycyl-L-histidyl-L-lysine manganese complex | 0.25% |
| propylene glycol | 0.56% |
| diazolidinyl urea | 0.30% |
| Methylparaben | 0.11% |
| Propylparaben | 0.03% |
| total | 100.00% |

Example 3

Stimulation of Collagen Formation in Fibroblasts by a Peptide Manganese Complex

The effect of peptide manganese complexes on collagen formation was determined by determining the amount of collagen type I produced by human fibroblasts in cell culture. Normal human dermal fibroblasts were seeded into a 96-well cell culture plate and grown to confluence in high glucose media supplemented with 10% fetal calf serum for 3 days. The fibroblasts were then placed in low glucose media with 2% serum and various amounts of a representative peptide manganese complex. After 3 days, the culture media was collected and analyzed for collagen type I content by a sandwich ELISA assay using purified antibody to collagen type I.

The results, shown in Table 4, show that the addition of GHK-Mn complex (glycyl-L-histidyl-L-lysine manganese) stimulated the formation of collagen type I.

TABLE 4

Stimulation of Collagen Type I Synthesis in Dermal Fibroblasts By Glycyl-L-Histidyl-L-Lysine Manganese Complex

| Concentration of Complex | ELISA Collagen Type I (% Increase) | Standard Deviation |
|---|---|---|
| 0 ug/ml control | 48 | ±4.2 |
| 10 ug/ml | 61.5 (+28%) | ±3.5 |
| 100 ug/ml | 102.5 (+129%) | ±0.7 |

Example 4

Stimulation of the Growth and Viability of Fibroblasts by a Peptide Manganese Complex The effect of peptide manganese complexes on the growth and viability of fibroblasts was determined. Normal human dermal fibroblasts were seeded into a 96-well cell culture plate and grown to confluence in high glucose media supplemented with 10% fetal calf serum for 3 days. The fibroblasts were then placed in low glucose media with 2% serum and various amounts of a representative peptide manganese complex. After 3 days, the cells were incubated with neutral red to assess their viability and stained with sulforhodamin B and counted to determine the number of cells.

The results, shown in Tables 5 and 6, show that the addition of GHK-Mn complex (glycyl-L-histidyl-L-lysine manganese) stimulated the proliferation of normal human dermal fibroblasts and increased their viability.

TABLE 5

Increase in Proliferation of Dermal Fibroblasts
By Glycyl-L-Histidyl-L-Lysine Manganese Complex

| Concentration of Complex | Sulforhodamin B Stain - Cell Number (% Increase) | Standard Deviation |
|---|---|---|
| 0 ug/ml control | 313 | ±6 |
| 10 ug/ml | 383 (+22%) | ±15 |
| 100 ug/ml | 535 (+71%) | ±5 |

TABLE 6

Increase in Viability of Dermal Fibroblasts
By Glycyl-L-Histidyl-L-Lysine Manganese Complex

| Concentration of Complex | Neutral Red Stain Stain - Cell Viability (% Increase) | Standard Deviation |
|---|---|---|
| 0 ug/ml control | 212 | ±12 |
| 10 ug/ml | 231 (+16%) | ±5 |
| 100 ug/ml | 253 (+19%) | ±19 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, it will be appreciated that, although specific embodiments of the present invention have been described herein for purposes of illustration, various modifications may be made without deviating from the spirit and scope of the invention. Accordingly, the present invention is not limited except as by the appended claims.

What is claimed is:

1. A method for treating photodamaged skin comprising contacting an area of skin in need thereof with an effective amount of a composition, wherein the composition comprises at least one peptide manganese complex selected from the group consisting of L-alanyl-L-histidyl-L-lysine:manganese (II) and L-valyl-L-histidyl-L-lysine:manganese(II).

2. The method of claim 1 wherein the at least one peptide manganese complex comprises L-alanyl-L-histidyl-L-lysine:manganese(II).

3. The method of claim 1 wherein the at least one peptide manganese complex comprises L-valyl-L-histidyl-L-lysine:manganese(II).

4. The method of claim 1 wherein the molar ratio of peptide to manganese in the at least one peptide manganese complex ranges from about 1:1 to about 3:1.

5. The method of claim 4 wherein the molar ratio of peptide to manganese in the at least one peptide manganese complex ranges from about 1:1 to about 2:1.

6. The method of claim 1 wherein the at least one peptide manganese complex is present at a concentration ranging from about 0.01% to about 5% by weight of the composition.

7. The method of claim 6 wherein the at least one peptide manganese complex is present at a concentration ranging from about 0.025% to about 1% by weight of the composition.

8. The method of claim 7 wherein the at least one peptide manganese complex is present at a concentration ranging from about 0.05% to about 0.5% by weight of the composition.

9. The method of claim 1 wherein the at least one peptide manganese complex is encapsulated in a liposome, microsponge or polymer matrix adapted to aid in the delivery of the peptide manganese complex to the area of skin or to enhance the stability of the composition.

10. The method of claim 1 wherein the at least one peptide manganese complex is formulated in an instrument adapted to deliver the peptide manganese complex to the area of skin via iontophoresis.

11. The method of claim 1 wherein the composition further comprises an inert and physiologically-acceptable carrier or diluent.

12. The method of claim 11 wherein the inert and physiologically-acceptable carrier or diluent is water, physiological saline, bacteriostatic saline, a petrolatum based cream, a pharmaceutically acceptable gel, a short chain alcohol, or a short chain glycol.

13. The method of claim 1 wherein the composition further comprises a skin lightening agent, a sunscreen agent, a skin conditioning agent, a skin protectant, an emollient, a humectant, or a mixture thereof.

14. The method of claim 1 wherein the composition further comprises a fatty alcohol, a fatty acid, an organic base, an inorganic base, a preserving agent, a wax ester, a steroid alcohol, a triglyceride ester, a phospholipid, a polyhydric alcohol ester, a fatty alcohol ether, a hydrophilic lanolin derivative, a hydrophilic beeswax derivative, a cocoa butter wax, a silicon oil, a pH balancer, a cellulose derivative, a hydrocarbon oil, or a mixture thereof.

15. The method of claim 1 wherein the composition further comprises an emulsifying agent, a surfactant, a thickening agent, an excipient, or a mixture thereof.

16. The method of claim 1 wherein the composition is in the form of a solution, cream, gel, fluid cream, lotion, or oil.

17. The method of claim 1 wherein the composition further comprises retinol, a retinol derivative, or a mixture thereof.

* * * * *